United States Patent [19]

Merrill, deceased et al.

[11] Plant 4,661

[45] Mar. 3, 1981

[54] PEACH TREE

[76] Inventors: Grant Merrill, deceased, late of Red Bluff, Calif.; Lucile B. Merrill, executrix, 325 Breese Ave., Red Bluff, Calif. 96080

[21] Appl. No.: 111,268

[22] Filed: Jan. 11, 1980

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is large, vigorous, spreading, foliated with large, oval-lanceolate leaves having a coarsely serrate margin, medium length petiole, and medium size, uniform glands positioned in opposition, blooms from large, obtuse to conic, plump, pubescent flower buds, the flowers being pink and of medium size, and a regular and productive bearer of uniform, symmetrical, globose, freestone fruit having yellow skin blushed and mottled with red, yellow flesh, and a medium size, beige stone.

1 Drawing Figure

BACKGROUND OF THE INVENTION

1. Field of the Invention

In an extensive plant breeding program, Grant Merrill, originator and now deceased, originated a large number of new and distinct varieties of fruit trees, and which included the herein-claimed variety of peach tree. Such plant breeding program was undertaken in originator's experimental orchard located near Exeter, Tulare County, Calif.

2. Prior Varieties

Among the existent varieties of peach trees which were known to originator, particular reference is made to Springcrest (unpatented) hereinafter mentioned for the purpose of comparison.

ORIGIN OF THE VARIETY

The present variety of peach tree was originated, in the aforesaid experimental orchard, as an open-pollinated seedling of an unknown variety.

ASEXUAL REPRODUCTION OF THE VARIETY

When such open-pollinated seedling matured as a bearing tree, and its novelty and commercial potential were recognized by originator, the variety was asexually reproduced by originator by grafting on suitable rootstock at a ranch located near Dinuba, Tulare County, Calif. The asexual reproduction of the variety ran true, in all respects, to the original tree of the variety.

SUMMARY OF THE VARIETY

The herein-claimed new and distinct variety of peach tree is large, vigorous, spreading, foliated with large, oval-lanceolate leaves having a coarsely serrate margin, medium length petiole, and medium size, uniform glands positioned in opposition, blooms from large, obtuse to conic, plump, pubescent flower buds, the flowers being pink and of medium size, and a regular and productive bearer of uniform, symmetrical, globose, freestone fruit having yellow skin blushed and mottled with red, yellow flesh, and a medium size, beige stone.

The herein-claimed new and distinct variety of peach tree is particularly characterized, in comparison with the Springcrest, by general similarity in tree and fruit but ripening of the fruit is approximately five to six days later.

BRIEF DESCRIPTION OF THE DRAWING

The drawing is an illustration, by photographic reproduction in color, depicting fruit of the variety; certain of such fruit being shown whole, while one is half cut away to expose the flesh and stone.

DESCRIPTION OF THE VARIETY

The obtanical details of this new and distinct variety of peach tree—with color definitions (except those in common color terms) referenced to Maerz and Paul Dictionary of Color (second edition)—are as follows:

Tree:
- *Size.*—Large.
- *Vigor.*—Vigorous.
- *Form.*—Spreading.
- *Production.*—Productive.
- *Bearing.*—Regular bearer.

Trunk:
- *Size.*—Stocky.
- *Texture.*—Medium.

Branches:
- *Size.*—Medium.
- *Texture.*—Medium.
- *Color.*—Brown (Falcon Muskrat — 8-J-10).
- *Lenticels.*—Number — numerous. Size — 1-2×4-5 mm.

Leaves:
- *Size.*—Large. Average length — 160 mm. Average width — 40 mm.
- *Form.*—Oval — lanceolate.
- *Color.*—Top side — medium green (Privet — 24-L-6). Under side — lighter green (Quaker Green — 23-H-5).
- *Margin.*—Coarsely serrate.
- *Petiole.*—Medium length (14 mm.). Medium thickness (2 mm.).
- *Glands.*—Average number — 2. Opposite. Medium size (1 mm.). Reniform. Green (Fern — 21-J-7).

Flower buds:
- *Size.*—Large.
- *Form.*—Obtuse to conic. Plump.
- *Pubescence.*—Pubescent.

Flowers:

*Blooming period.*—Date of first bloom — March 3rd. Date of approximate full bloom (90%) — March 11th. Petal fall — March 16th. Medium, as compared with other varieties.

*Size.*—Medium (20 mm. in diameter).

*Color.*—Top side — Pink (49-D-1). Under side — Pink (49-E-1).

*Pistils.*—Number — 1.

Stamens.—Number — 38-39.

Fruit:

*Maturity when described.*—Hard.

*Date of first picking.*—May 29, 1979.

*Date of last picking.*—June 5, 1979.

*Size.*—Uniform. Medium. Average diameter axially — 68 mm. Average transversely in suture plane — 69 mm.

*Form.*—Symmetrical. Globose.

*Suture.*—Distinct. Shallow, but deepening at apex, with slight depression beyond pistil point.

*Ventral surface.*—Rounded slightly.

*Cavity.*—Flaring.

*Base.*—Rounded.

*Apex.*—Rounded. Depressed.

*Pistil point.*—Cuspidate.

*Stem.*—Average length — 10 mm. Average caliper — 5 mm.

Skin:

*Thickness.*—Medium.

*Texture.*—Medium.

*Tendency to crack.*—None.

*Down.*—Scant.

*Color.*—Ground color — Yellow (Capucine — 9-K-8). Slightly lighter yellow along suture line. Blush — Red (Kazak-Coptic — 7-L-9).

Flesh:

*Color.*—Yellow (Cavalry Deep Chrome YP — 9-L-7). Surface of pit cavity — Yellow (Cadmium — 9-L-8).

*Juice.*—Abundant.

*Texture.*—Fine. Melting.

*Fibers.*—Few. Fine.

*Ripens.*—Evenly.

*Flavor.*—Sub-acid.

*Aroma.*—Distinct.

*Eating quality.*—Good.

Stone:

*Type.*—Free.

*Size.*—Medium. Average length — 28 mm. Average breadth — 21 mm. Average thickness — 16 mm.

*Form.*—Oval.

*Base.*—Straight.

*Hilum.*—Narrow.

*Apex.*—Acute.

*Sides.*—Equal.

*Surface.*—Irregularly furrowed toward apex. Pitted toward base.

*Ridges.*—Rounded.

*Pits.*—Circular — elongated.

*Ventral edge.*—Thin, with wing toward base.

*Dorsal edge.*—Full, with broad groove throughout.

*Color.*—Beige (Leghorn — 10-D-3).

*Tendency to split.*—Slight.

Use: Market; dessert.

Keeping quality: Good.

Shipping quality: Good.

The peach tree and its fruit herein described may vary in slight detail due to climatic and soil conditions under which the variety may be grown; the present description being of the variety as grown in the Central Valley of California.

It is claimed:

1. A new and distinct variety of peach tree, substantially as illustrated and described, which is particularly characterized by general similarity, in tree and fruit, to the Springcrest but ripening of the fruit is approximately five to six days later.

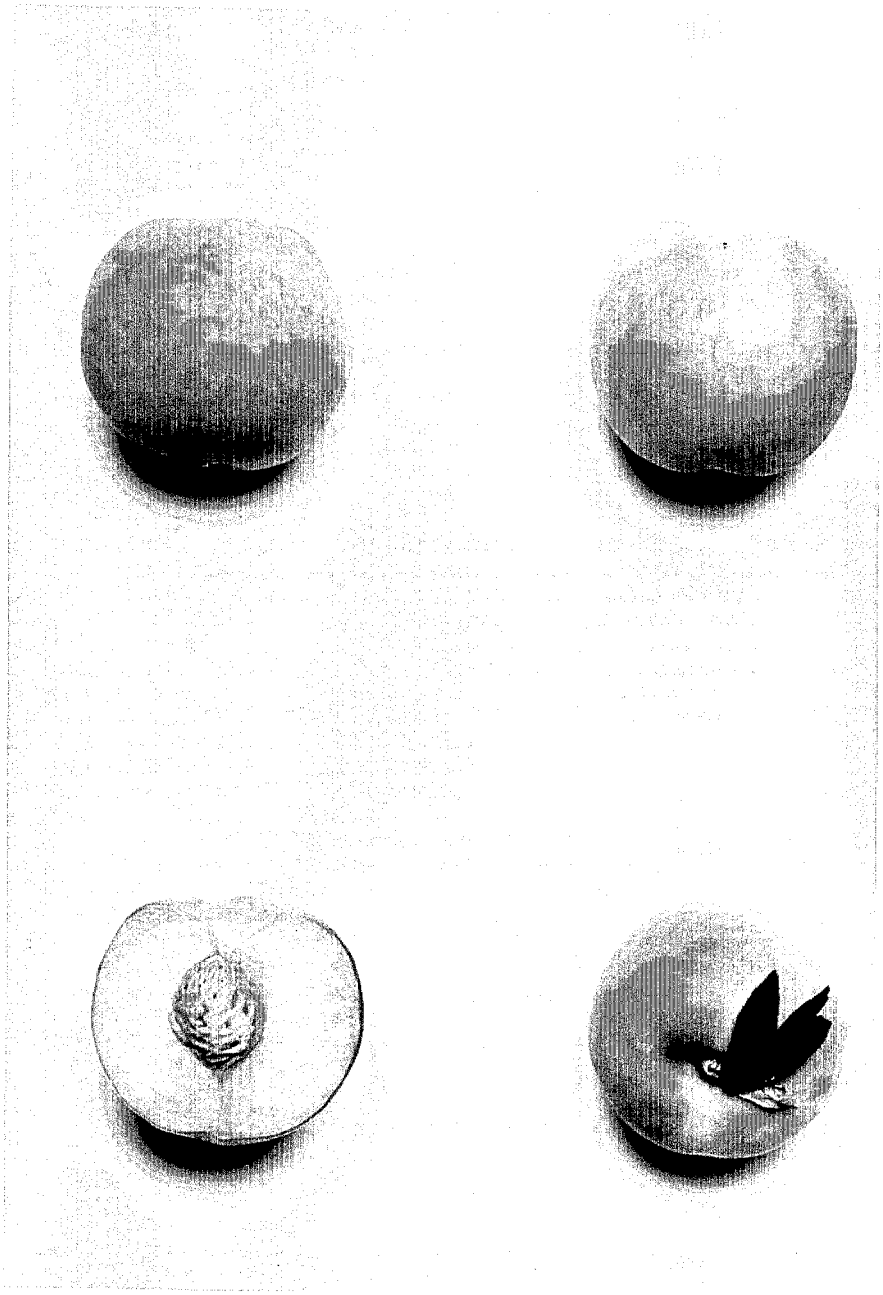

* * * * *